(12) United States Patent
Saltzman et al.

(10) Patent No.: US 6,322,815 B1
(45) Date of Patent: Nov. 27, 2001

(54) MULTIPART DRUG DELIVERY SYSTEM

(76) Inventors: W. Mark Saltzman, 1017 Dartmouth Glen, Baltimore, MD (US) 21212; O. Michael Colvin, 7310 Yorktowne Dr., Baltimore, MD (US) 21204; Wenbin Dang, 3 Viking Ct., Apartment 26, Arlington, MA (US) 02174; Susan Ludeman, 15 Chase Mill Cir., Owings Mills, MD (US) 21117

( * ) Notice: Subject to any disclaimer, the term of this patent is extended or adjusted under 35 U.S.C. 154(b) by 0 days.

(21) Appl. No.: 08/279,302

(22) Filed: Jul. 22, 1994

(51) Int. Cl.$^7$ ................................ A61K 9/14; A61K 9/22; A61K 9/00
(52) U.S. Cl. ........................ 424/486; 424/400; 424/423; 424/468; 424/486; 424/487; 424/488
(58) Field of Search ................................ 424/468, 486, 424/487, 488, 400, 423

(56) References Cited

U.S. PATENT DOCUMENTS

| | | |
|---|---|---|
| 4,195,017 | 3/1980 | Bogoch . |
| 4,196,186 | 4/1980 | Bogoch . |
| 4,699,784 * | 10/1987 | Shih et al. .......................... 530/391 |
| 4,701,521 * | 10/1987 | Ryser et al. ......................... 530/322 |
| 4,844,897 * | 7/1989 | Maeda et al. ....................... 424/94.3 |
| 4,894,238 | 1/1990 | Embry et al. . |
| 4,975,280 | 12/1990 | Schacht et al. . |
| 4,976,962 | 12/1990 | Bichon et al. . |
| 4,996,047 | 2/1991 | Kelleher et al. . |
| 5,051,257 | 9/1991 | Pietronigro . |
| 5,053,228 | 10/1991 | Mori et al. . |
| 5,130,126 | 7/1992 | Koyama et al. . |

OTHER PUBLICATIONS

Brem et al., "Interstitial Chemotherapy with Drug Polymer Implants for the Treatment of Recurrent Gliomas", *J. Neurosurg.* 74:441–446 (1991).

Chasin et al., "Interstitial Drug Therapy for Brain Tumors: A Case Study", *Drug Development and Industrial Pharmacy*, 16(18):2579–2594 (1990).

Dang et al., "Covalent Coupling of Methotrexate to Dextran Enhances the Penetration of Cytotoxicity into a Tissue–like Matrix", *Cancer Research* 54:1729–1735 (1994).

Dang et al., "Dextran Retention in the Rat Brain Following Release From a Polymer Implant", *Biotechnol. Prog.*, 8:527–532 (1992).

Grossman et al., The Intracerebral Distribution of BCNU Delivered by Surgically Implanted Biodegradable Polymers, *J. Neurosurg.* 76:640–647 (1992).

Powell et al. "Controlled Release of Nerve Growth Factor From a Polymeric Implant", *Brain Res.* 515:309–311 (1990).

Radomsky et al., "Controlled Vaginal Delivery of Antibodies in the Mouse", *Biol. of Reprod.*, 47:133–140 (1992).

Reinhard et al., "Polymeric Controlled Release of Dexamethasone in Normal Rat Brain", *Journal of Controlled Release* 16:331–340 (1991).

(List continued on next page.)

*Primary Examiner*—Thurman K. Page
*Assistant Examiner*—S. Tran
(74) *Attorney, Agent, or Firm*—Banner & Witcoff

(57) ABSTRACT

Polymeric drug conjugates in controlled release matrices are provided which allow sustained concentrations of therapeutic agents within a treated area for a prolonged period. The polymeric drug conjugates hydrolytically degrade in the extracellular space in a controlled, pre-specified pattern, releasing active drug. The conjugates diffuse within the tissue reaching a greater distance from the matrix than free drug would, because of their reduced rate of clearance from the tissue via the capillary system.

10 Claims, 10 Drawing Sheets

OTHER PUBLICATIONS

Saltzman, "Antibodies for Treating and Preventing Disease: The Potential Role of Polymeric Controlled Release", *Critical Reviews in Therapeutic Drug Carrier Systems*, 10(2):11–142 (1993).

Saltzman et al., "Controlled Antibody Release From a Matrix of Poly(Ethylene–co–Vinyl Acetate) Fractionated With a Supercritical Fluid", *Journal of Applied Polymer Science*, 48:1493–1500 (1993).

Saltzman et al., "Drugs Released From Polymers: Diffusion and Elimination in Brain Tissue", *Chemical Engineering Science*, 46(10):2429–2444 (1991).

Saltzman et al., "Transport Rates of Proteins in Porous Materials With Known Microgeometry", *Biophys. J.*, 55:163–171 (1989).

Sherwood et al., "Controlled Antibody Delivery Systems", *Biotechnology 10*:1446–1449 (1992).

Tamargo et al., "Interstitial Delivery of Dexamethasone in the Brain for the Reduction of Peritumoral Edema", *J. Neurosurg 74*:956–961 (1991).

Yang et al., "Controlled Delivery of 1,3–Bix(2–chloroethyl)–1–Nitrosourea From Ethylene–Vinyl Acetate Copolymer", *Cancer Research 49*:5103–5107 (1989).

* cited by examiner

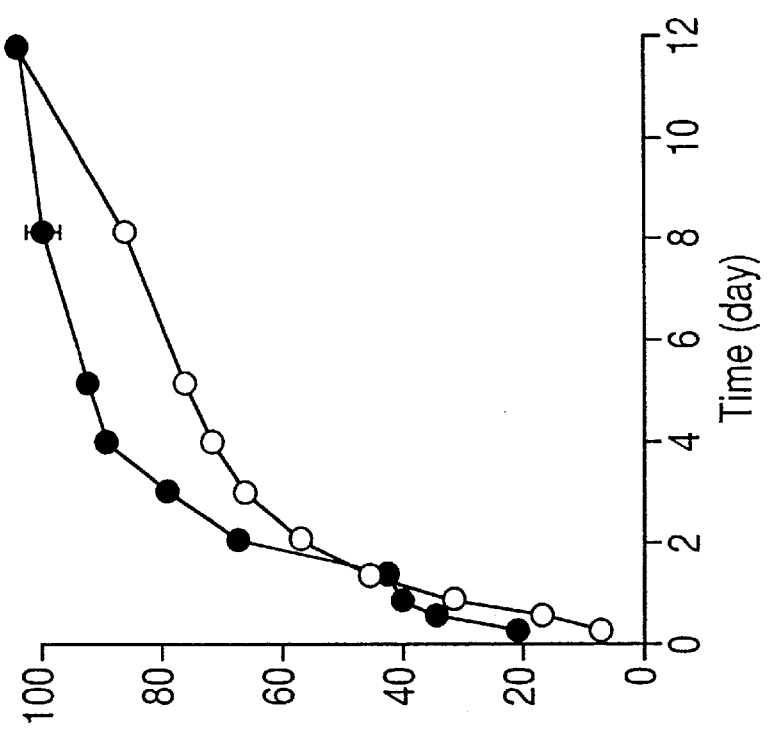
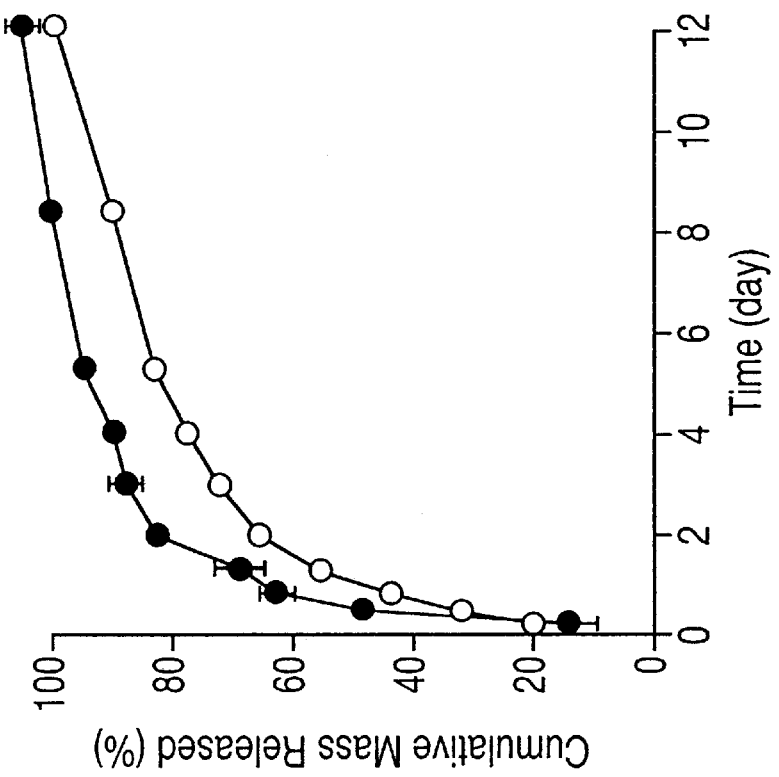

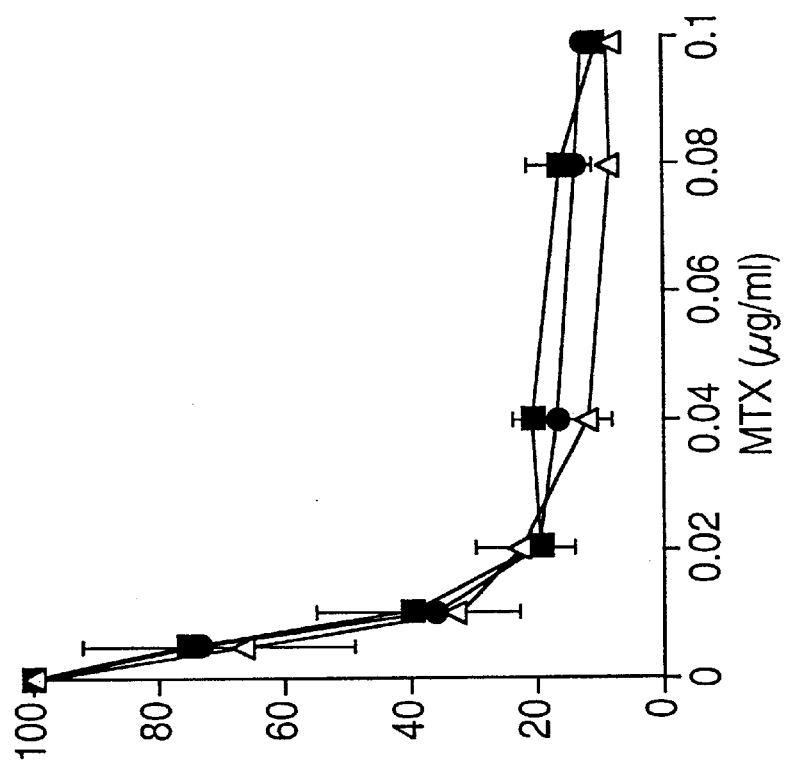
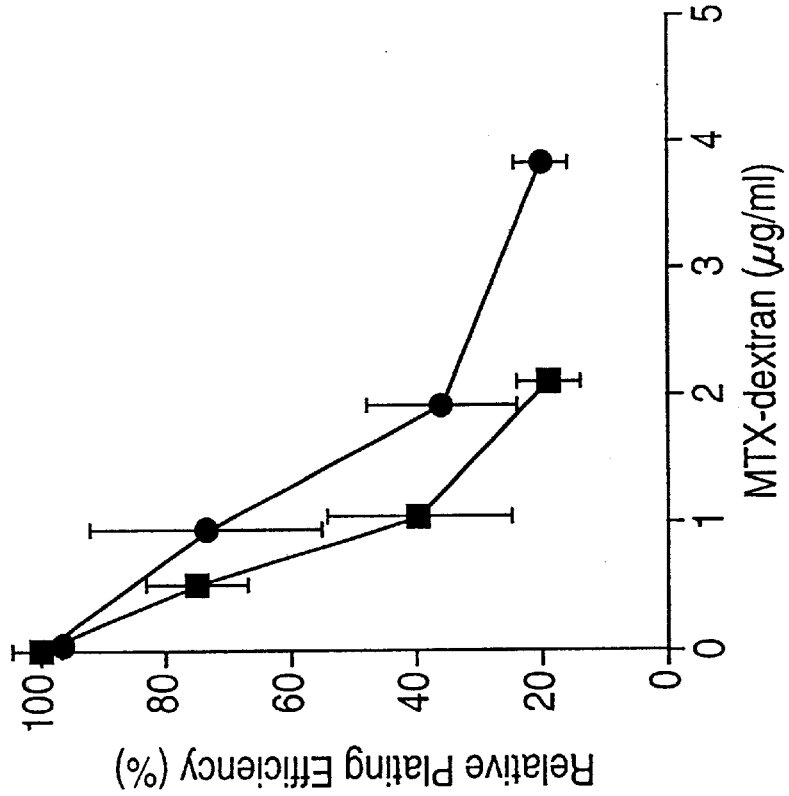

MULTIPART DRUG DELIVERY SYSTEM

BACKGROUND OF THE INVENTION

The blood-brain barrier, which results from the low permeability of brain capillaries to most drug molecules, prevents systemically delivered agents from reaching the parenchymal tissue of the brain. Because of this barrier, conventional modes of drug delivery often fail to provide therapeutic drug doses to the brain. Recently, implantable or injectable polymeric controlled release systems have been developed for achieving high concentrations of agents within the brain tissue over an extended period of time (Sabel, et al., 1989, *Annals of Neurology*, 25:351–356; Saltzman, et al., 1991, *Chemical Engineering Science*, 46:2429–2444; Reinhard, et al., 1991, *Journal of Controlled Release*, 16:331–340; Brem, et al., 1991, *Journal of Neurosurgery*, 74:441–446; Powell, et al., 1990, *Brain Research*, 515:309–311). Controlled release polymers are designed to release precisely defined quantities of agents over an extended period. When these polymeric systems are inserted directly into the brain tissue, they release a biologically active agent into the brain extracellular space—already past the blood-brain barrier—where they can diffuse within the tissue and provide their therapeutic effect.

While controlled release may be important for treating certain disease of the brain with some specific agents, it has important limitations. Therapeutic agents are released into the brain extracellular space. To be effective, the released agent must diffuse within the extracellular space to reach its site of action. In many cases, this site of action may be many millimeters or centimeters from the polymer matrix. Unfortunately most agents of interest will be removed from the brain by the capillary system or destroyed by brain metabolic processes before they can diffuse far enough to be effective. For example, five chemotherapeutic compounds (hydroxyurea, MTX, thiotepa, BCNU, and cytosine arabinoside) penetrated only 1–5 mm from the ependymal surface following intrathecal perfusion (Blasberg, et al., 1975, *J. Pharmacol. Exp. Ther.*, 195:73–83). Autoradiography following surgically implantation of degradable radiolabeled BCNU-loaded polymers in rabbits revealed that the bulk of the BCNU was within several mm of the implant site (Grossman, et al., 1992, *J. Neurosurg.*, 76:640–647). Similarly, the diffusion distance for cisplatin was <1 mm following direct microinfusion in the rat brain (Morrison, et al., 1986, *J. Pharm. Sci.*, 75:120–128). These small penetration distances for anticancer drugs in brain tissue may limit the effectiveness of polymer matrices for tumor therapy. This limitation may be particularly significant for the treatment of glioblastoma, which can recur several cm from the original primary tumor site (Hochberg, et al., 1980, *Neurology* 30:907–911).

Thus there is a need in the art for drug delivery vehicles which achieve a larger area of penetration of drug than simple drug-releasing polymer matrices.

SUMMARY OF THE INVENTION

It is an object of the invention to provide an implantable multipart drug delivery system having a reduced rate of drug elimination from its target tissue and an enhanced penetration volume from its implantation site relative to free drug.

It is another object of the invention to provide a method of treating a human having a brain disease.

It is yet another object of the invention to provide a drug-polymer conjugate for delivering free drug to the extracellular space of a tissue with a reduced rate of elimination.

It is still another object of the invention to provide a method for administering intrathecal therapy.

These and other objects of the invention are provided by one or more of the embodiments described below. In one embodiment of the invention an implantable multipart drug delivery system is provided. The system provides a reduced rate of drug elimination from its target tissue and an enhanced penetration volume from its implantation site relative to free drug. The system comprises:

(a) a drug covalently attached via a hydrolytically labile bond to (b) a water soluble, high molecular weight first polymer, forming a first drug-polymer conjugate, said conjugate being incorporated in (c) a controlled-release matrix comprising a biocompatible second polymer.

In another embodiment of the invention a method of treating a human having a brain disease is provided. The method comprises: implanting into the brain of said human a multipart drug delivery system having a reduced rate of drug elimination from its target tissue and an enhanced penetration volume from its implantation site relative to free drug. The multipart drug delivery system comprises: (a) a drug covalently attached via a hydrolytically labile bond to (b) a water soluble, high molecular weight first polymer forming a first drug-polymer conjugate, said conjugate being incorporated in (c) a controlled-release matrix comprising a biocompatible second polymer.

In still another embodiment of the invention a method of performing intrathecal therapy is provided. The method comprises the step of:

administering directly to an intrathecal space a drug-polymer conjugate, said drug-polymer conjugate providing a reduced rate of drug elimination from its target tissue relative to free drug, said drug-polymer conjugate comprising: (a) a drug attached via an hydrolytically labile bond to (b) a water-soluble, high molecular weight polymer.

These and other embodiments of the invention provide the art with the means to treat more effectively localized and disseminated diseases which respond to sustained exposure to therapeutic agents.

BRIEF DESCRIPTION OF THE DRAWINGS

FIG. 6. Biological activity of released MTX from p(FAD:SA) pellets. The amount of MTX released from p(FAD:SA) containing MTX-amide-dextran FIG. 6(a) or MTX-ester-dextran FIG. 6(b) was analyzed by an enzyme inhibition assay (●) and compared with the value obtained by UV absorbance at 305 nm (○). Points, mean value obtained for three identical polymer pellets. Bars, SD.

FIG. 7. Cytotoxicity of MTX (Δ), MTX-amide-dextran (■), and MTX-ester-dextran (●) against H80 cells in culture. Concentrations are expressed as total concentration of drug or drug conjugate FIG. 7(a) or as equivalents of MTX FIG. 7(b). Points, mean value obtained from experiments in three identical wells. Bars, SD.

DETAILED DESCRIPTION OF THE INVENTION

Figure 1:
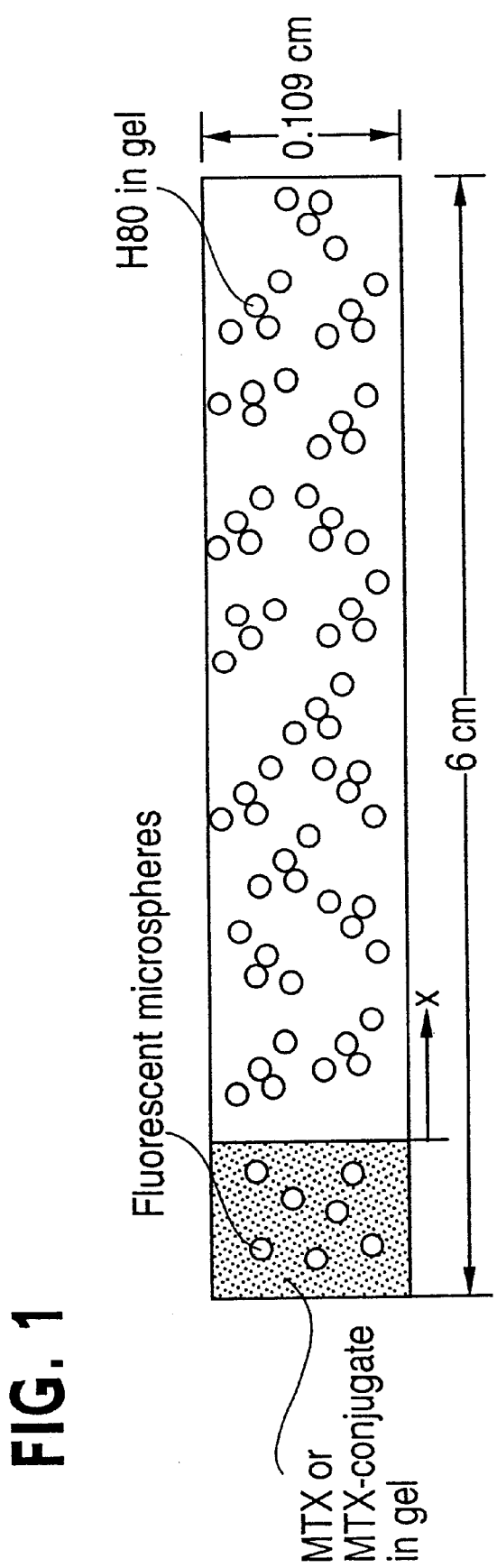
FIG. 1. Schematic diagram of three-dimensional cell culture within a hollow fiber. H80 cells were suspended in agarose gel and filled the lumen of the hollow fiber. A second agarose gel containing dissolved MTX or MTX-dextran was placed at one end of the fiber. Fluorescence microspheres were mixed with the drug source to identify the interface between drug- and cell-containing regions.

It is a discovery of the present invention that conjugation of a drug to a water-soluble polymer via a hydrolytically labile bond increases drug retention in a tissue, and, therefore, increases the drug penetration distance in the tissue. Typically the drug conjugate is administered in a controlled-release matrix which comprises a biocompatible second polymer, typically not water-soluble. The drug delivery system (drug conjugate in controlled release matrix) can be implanted during surgery or stereotactically injected.

According to the present invention, active agents (drugs) are modified by chemically linking them to a high molecular weight, water-soluble polymer carrier. This modified agent is termed herein a drug-polymer conjugate. One special property of the drug conjugate is that the chemical linkage of the agent to the water-soluble polymer will hydrolytically degrade, releasing biologically active agent into the extracellular space.

The drug-polymer conjugates can be incorporated into a controlled release matrix, formulated from a second biocompatible polymer. When implanted into a tissue such as the brain, the controlled-release matrix will release the drug-polymer conjugate which will release free drug molecules to treat the area of the tissue in the immediate vicinity of the polymer. The drug-polymer conjugates will also diffuse within the tissue, reaching a great distance from the matrix because of their low rate of clearance from the tissue. (The low elimination rate is due to the inability of capillaries to absorb molecules of such a high molecular weight.) As the drug conjugates diffuse, the bond between the polymer and the drug will slowly degrade in a controlled, prespecified pattern, releasing the active agent into the extracellular space to have its therapeutic effect. Similarly, drug-polymer conjugates can be administered directly to a tissue and the elimination rate will be reduced relative to free drug. This is particularly useful for intrathecal administration of drugs, where the rate of drug elimination is often the limiting factor in achieving an effective therapeutic dosage.

There are several important variables, all of which can be controlled to produce a final product that is best suited for treating a certain disease with specific kinds of agents:

i) The size and characteristics of the water-soluble polymer carrier can be varied. Either synthetic or naturally occurring polymers may be used. While not limited to this group, some types of polymers that might be used are polysaccharides (e.g. dextran, ficoll), proteins (e.g. poly-lysine), poly(ethylene glycol), or poly (methacrylates). Different polymers, because of their different size and shape, will produce different diffusion characteristics in the target tissue or organ. The therapeutic value of the drug delivery system may be further improved by using as the water-soluble polymer antibody molecules directed against cell surface antigens of selected target cells. In this case the antibody-based polymeric drug-polymer conjugate will be retained for an extended period within the extracellular space, and—while in the extracellular space—will specifically bind to the target cells.

ii) The nature of the hydrolytically labile bond between the water-soluble polymer and the drug can be varied. While not wishing to be limited to the following bonds, we have chemically bonded drugs to water-soluble polymers using covalent bonds, such as ester, amide, amidoester, and urethane bonds. We have also produced ionic conjugates. We have discovered that by changing the nature of the chemical association between water-soluble polymer and drug, the half-life of carrier-drug association can be varied. This half-life of the drug-polymer conjugate in the extracellular space will determine the rate of active drug release from the polymer and, therefore, the degree of penetration that the drug-polymer conjugate can achieve in the target tissue. Other suitable hydrolytically labile bonds which can be used to link the drug to the water soluble polymer include thioester, acid anhydride, carbamide, carbonate, semicarbazone, hydrazone, oxime, iminocarbonate, phosphoester, phophazene, and anhydride bonds.

The rate of hydrolytic degradation, and thus of drug release, can be altered from minutes to months by altering the physico-chemical properties of the bonds between the drugs and the polymer. The rate of release can be affected by (a) the nature of the bond, e.g., ionic, thioester, anhydride, ester, and amide links, in order of decreasing lability; (b) stereochemical control, building in varying amounts of steric hindrance around the bonds which are to be hydrolyzed; (c) electronic control, building in varying electron donating/accepting groups around the reactive bond, controlling reactivity by induction/resonance; (d) varying the hydrophilicity/hydrophobicity of spacer groups between the drug and the polymer; (e) varying the length of the spacer groups, increasing length making the bond to be hydrolyzed more accessible to water; and (f) using bonds susceptible to attack by enzymes present in the extracellular matrix or on the surface of cells.

iii) The properties of the controlled release matrix can be varied, according to methods described in previous publications (Saltzman, et al., 1991, *Chemical Engineering Science*, 46:2429–2444; Powell, et al., 1990, *Brain Research*, 515:309–311; Dang, et al., 1992, *Biotechnology Progress*, 8:527–532; Saltzman, et al., 1989, *Biophysical Journal*, 55:163–171; Radomsky, et al., 1992, *Biology of Reproduction*, 47:133–140; Saltzman, et al., 1992, *Journal of Applied Polymer Science*, 48:1493–1500; Sherwood, et al., 1992, *Bio/Technology*, 10: 1446–1449), to vary the rate of polymeric drug conjugate release into the tissue. Among the variables which affect conjugate release kinetics are: controlled release polymer composition, mass fraction of drug-polymer conjugate within the matrix (increasing mass fraction increases release rate), particle size of drug-polymer conjugate within the matrix (increasing particle size increases release rate), composition of polymeric drug conjugate particles (which can be varied by adding free drug agents or inert agents that influence particle solubility), and size (increasing surface area increasing the release rate), and shape (changing the pattern, e.g., first order, zeroth order, etc.) of the controlled release matrix. Suitable polymers for use as controlled-release matrices include poly (ethylene-co-vinyl acetate), poly(DL-lactide), poly (glycolide), copolymers of lactide and glycolide, and polyanhydride copolymers.

The polymer-drug conjugate and drug delivery system of the present invention are particularly useful for treatment of brain diseases such as tumors (gliomas, astrocytomas, metastases from tumors of other organs, etc.) Alzheimer's disease, Parkinson's disease, neurodegenerative diseases, seizure disorders, psychiatric-disorders, etc. Localized diseases in other tissues are also suitable targets for the drug-polymer conjugate and the drug delivery system. Tumors in other parts of the body can be treated, as can other localized lesions. Drugs which are suitable for conjugation includes cytotoxic agents, nucleotide analogs, healing factors, antibiotics, hormones, neurotransmitters, growth factors, cytokines, trophic factors, etc.

According to particular embodiments of the invention, other components can be incorporated into the controlled-release matrix, in addition to the drug-polymer conjugate. In some instances free drug molecules are also incorporated to provide a rapid release of active drug at the site of implantation. In other cases, different drug-polymer conjugates are incorporated into the same controlled-release matrix. The drug-polymer conjugates can vary by the type of hydrolytically labile bond, or by the identity of the first polymer used in the conjugate. Using combinations of drug-polymer conjugates one can achieve a broader spectrum of diffusion distances and elimination rates.

As shown in more detail below, it has now been shown that conjugation of an anticancer drug to a water-soluble macromolecule via an hydrolytically labile bond increases drug retention in brain tissue, and, therefore, increases the drug penetration distance in the brain. Polymeric anticancer drug conjugates might find their greatest use in the eradication of occult tumor cells that remain after the removal of primary tumors. For example, a biodegradable polymer pellet containing the mixture of free drug and polymeric drug conjugate could be implanted into a desired location of the brain after the removal of tumor. In this way, free drug can kill tumor cells in the vicinity of the polymer quickly, while drug conjugates provide active drug for a prolonged time at a greater distance from the polymer, killing tumor cells over a larger volume at tolerable doses.

EXAMPLES

Example 1

This example demonstrates the synthesis and characterization of drug-polymer conjugates.

Figure 2B:
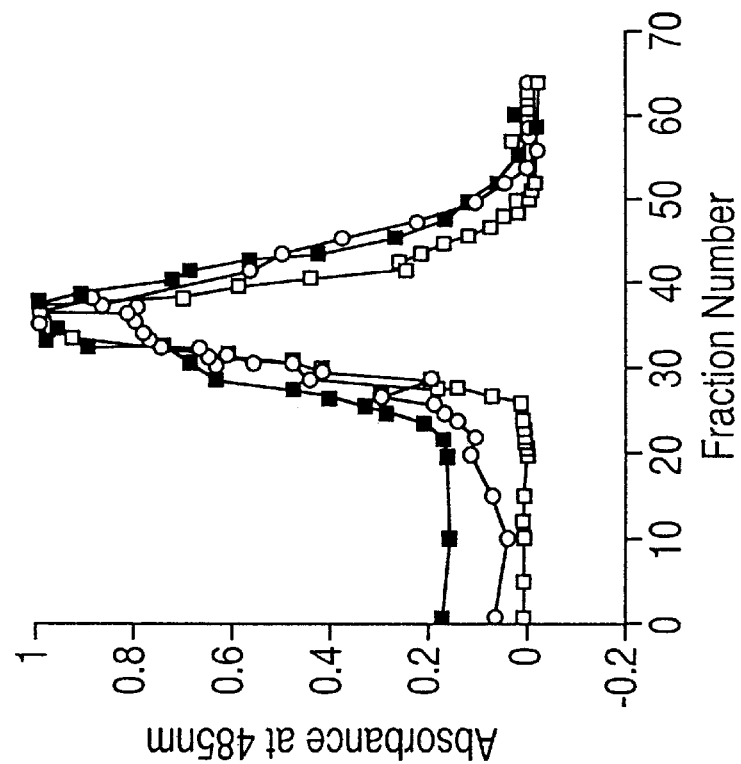
FIG. 2*b*, molecular weight distributions for $M_r$ 70,000 dextran (■), MTX-amide-dextran (□), and MTX-ester-dextran (○). Solutions of dextran or MTX-dextran were passed through the column, and 2-ml fractions were collected. Dextran concentration in each fraction was analyzed by a carbohydrate assay. Absorbance at 485 nm represents the concentration of dextran in each fraction.
Figure 2A:
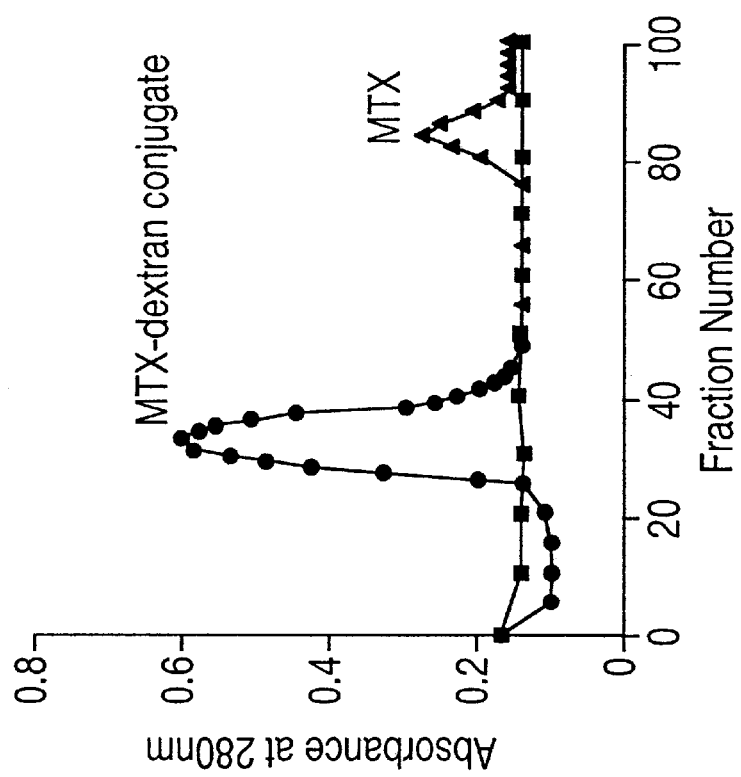
FIG. 2*a*, gel filtration patterns for MTX-dextran conjugate (●), $M_r$ 70,000 dextran (570), and MTX (▼) on a HiLoad 16/60 Sephacryl S-200 gel filtration column. The elution was monitored by UV absorbance at 280 nm.

Methotrexate-dextran (MTX-dextran) conjugates were produced by several techniques. The reaction mixture of MTX with oxidized dextran (polyaldehyde-dextran) and unreacted dextran-70 were applied to gel filtration columns and eluted with PBS. Elution profiles were obtained by monitoring absorbance at 280 nm, which revealed no absorbance for dextran at 280 nm, as expected, and two peaks for MTX-dextran conjugate (FIG. 2a). To monitor the elution profile of dextran, dextran concentrations in each eluted fraction were measured (FIG. 2b). There was no change in the molecular weight distribution of dextran after the conjugation reaction. In addition, the elution peak of $M_r$ 70,000 dextran matched the first elution peak for MTX in FIG. 2a, suggesting that MTX was covalently linked to dextran. The second peak in FIG. 2a was attributed to unconjugated MTX.

Figure 3:
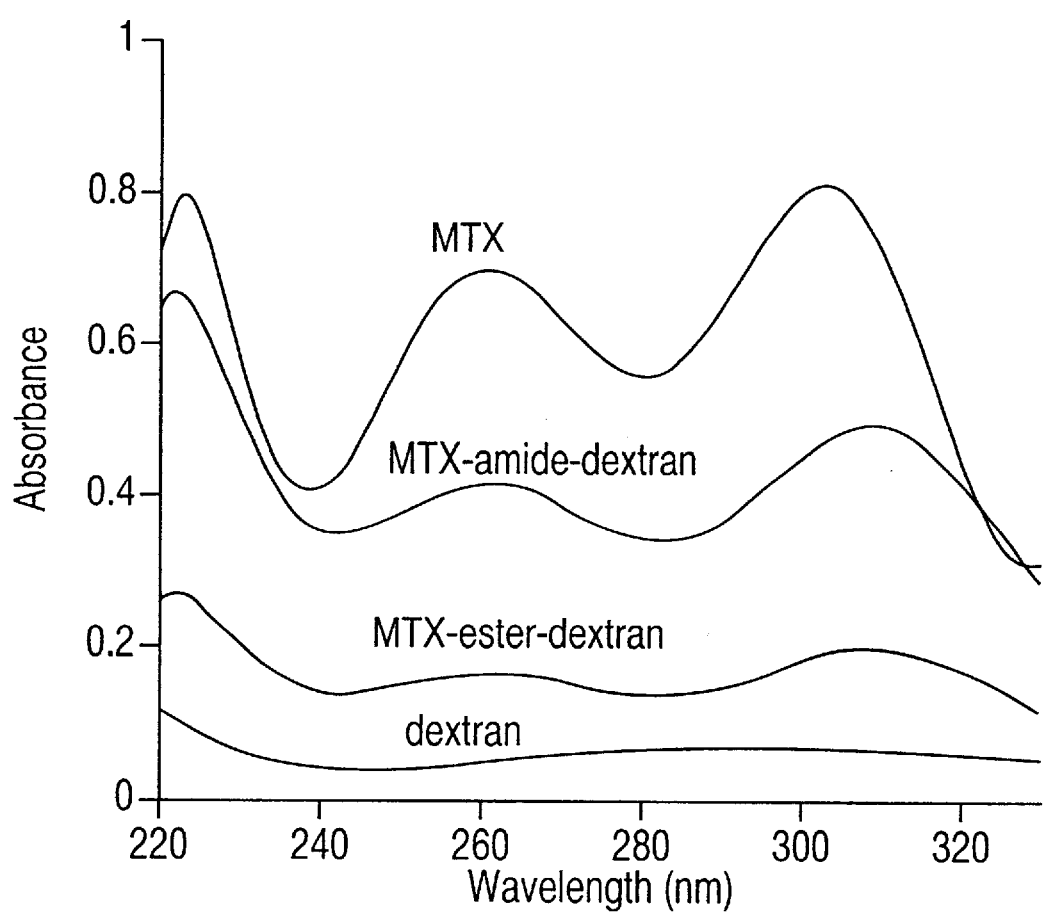
FIG. 3. UV spectra for dextran, MTX, and MTX-dextran conjugates. The characteristic peaks of MTX remained after conjugation of MTX to dextran via either the amide or ester linkage. The differences in absorbance were attributable to differences in MTX concentrations.

For PBS solutions containing MTX or MTX-dextran conjugate, characteristic UV absorbance peaks at 305 nm (primarily due to the aminobenzoyl group) and 258 nm (due to both the diaminopteridine moiety and aminobenzoyl group) (Chamberlin, A. R., 1976, Methotrexate, In: *Analytical Profiles of Drug Substances*, Florey (eds.), New York: Academic Press) were observed (FIG. 3). The UV spectra of MTX-dextran conjugates were similar to unreacted MTX, indicating no significant alteration in the structural properties of the MTX molecule during conjugation. For MTX-dextran conjugates, these spectra were obtained from eluted fractions containing the maximum amount of dextran (i.e., fractions corresponding to the peak in FIG. 2b), further suggesting that MTX was covalently linked to dextran.

Figure 4:
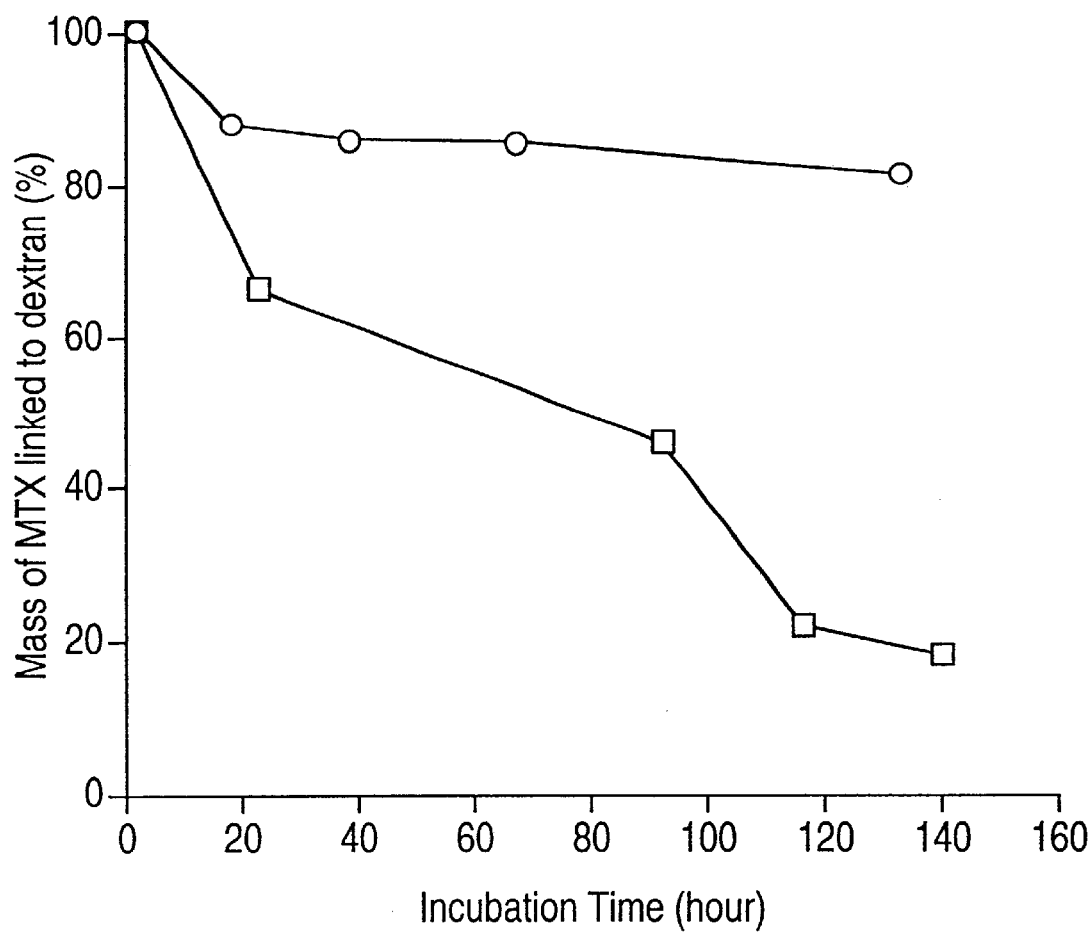
FIG. 4. Dissociation of MTX from MTX-dextran conjugates during incubation in PBS at 37° C. MTX-amidedextran (○) or MTX-ester-dextran (□) were incubated in PBS at 37° C. for various periods of time, and the amount of MTX associated with dextran was determined by the area under the peak obtained by gel filtration chromatography (as in FIG. 2a).

When MTX-dextran conjugates were incubated in PBS, the rate of MTX dissociation from the dextran carrier depended on the linkage chemistry (FIG. 4). The MTX-amide-dextran was fairly stable ($t_{1/2}$>20 days), while the MTX-ester dextran conjugate had a dissociation half-life of ~3 days in PBS at 37° C.

Methods: MTX and dextran ($M_r$ 70,000) were from Sigma Chemical Company (St. Louis, Mo.). MTX was covalently linked to dextran-70 via spacers with terminal —NH$_2$ or —OH moiety based on the methods of Chu and Whitely (Chu, et al., 1977, *Mol. Pharmacol.*, 13:80–88) and Onishi and Nagai (Onishi, et al., 1986, *Chem. Pharm. Bull.* (Tokyo), 34:2561–2567) with modifications. Dextran was first oxidized to a polyaldehyde by sodium periodate (Molteni, L., 1979, Dextrans as carriers, In: *Drug Carriers*

*in Biology and Medicine*, G. Gregoriadis (eds.), New York: Academic Press). Ten g of dextran were dissolved in 100 ml of distilled water. Sodium periodate (2.635 g) was added to the dextran solution and maintained at room temperature for 1 h in the dark with constant stirring. The reaction was terminated by the addition of 7.654 g of ethylene glycol and further maintained in the dark for 1 h. The mixture was dialyzed against distilled water for 2 days at 4° C. Either diaminohexane (2.553 g) or 5-amino-1-pentanol (2.553 g) was added to the above solution, and the pH was adjusted to 9.0 with 1 M NaOH and HCl solutions. This reaction proceeded for 6 h before 6.8 g sodium borohydride was added. The reaction mixture was kept overnight (pH 9.5) at room temperature, followed by addition of an additional 2.8 g of sodium borohydride. This reaction was maintained for another 8 h (pH 9.5). The reaction mixture was then dialyzed against distilled water for 2 days at 4° C., and the solution was lyophilized. For the final conjugation of MTX, 300 mg of modified dextran [dextran-$(CH_2)_6$—$NH_2$ or dextran-$(CH_2)_5$—OH] were dissolved in 10 ml of distilled water followed by addition of 5 mg of MTX and 300 mg of 1-ethyl-3-(3-dimethylaminopropyl)carbodiimide hydrochloride. The pH of the solution was adjusted to 6.0 with 1 N NaOH and 1 N HCl. The mixture was stirred for 24 h in the dark at room temperature. The mixture was further dialyzed at 4° C. for 1 day and ultra filtered (molecular weight cut-off of 30,000) and finally freeze-dried to obtain MTX-dextran conjugates.

The polymeric drug conjugates were characterized for: (a) properties of dextran carrier (molecular weight distribution); and (b) properties of MTX. Dextran before conjugation and MTX-dextran conjugates were dissolved in PBS (pH 7.4, 120 mM NaCl-2.7 mM KCl-10 mM phosphate with 0.02% gentamicin; Sigma). These solutions were passed through a HiLoad 16/60 Sephacryl S-200 gel filtration column (Pharmacia) using a P-500 pump (Pharmacia) at a speed of 0.5 ml/min and monitored by UV absorbance at 280 nm. Fractions of 2 ml elution were collected using a Frac-100 fraction collector (Pharmacia). Each fraction was analyzed for the concentration of dextran by an assay for carbohydrate (Dubois, et al., 1956, *Anal. Chem.*, 28:350–356), which was modified slightly. The molecular weight distribution of dextran before and after conjugation was compared. The UV scans of MTX-dextran from fractions containing the maximum amount of dextran were compared with the UV spectrum of pure MTX to determine if there were any alterations in the structural properties of the MTX molecule.

Known quantities of MTX-dextran were dissolved in 1 ml of PBS and incubated at 37° C. for various time periods. Solutions before and after incubation were passed through a HiLoad 16/60 Sephacryl S-200 gel filtration column (Pharmacia) at 0.5 ml/min using a P-500 pump (pharmacia) and monitored by UV absorbance at 280 nm. The amount of MTX attached to dextran, before and after incubation, was proportional to the area under the peak at elution volume ~60 ml (corresponding to $M_r$ 70,000 dextran). The half-life of MTX dissociation from the dextran carrier was calculated as the time required for dissociation of 50% of MTX from dextran.

Example 2

This example demonstrates the controlled release of drug-polymer conjugates in vitro.

Figure 5B:
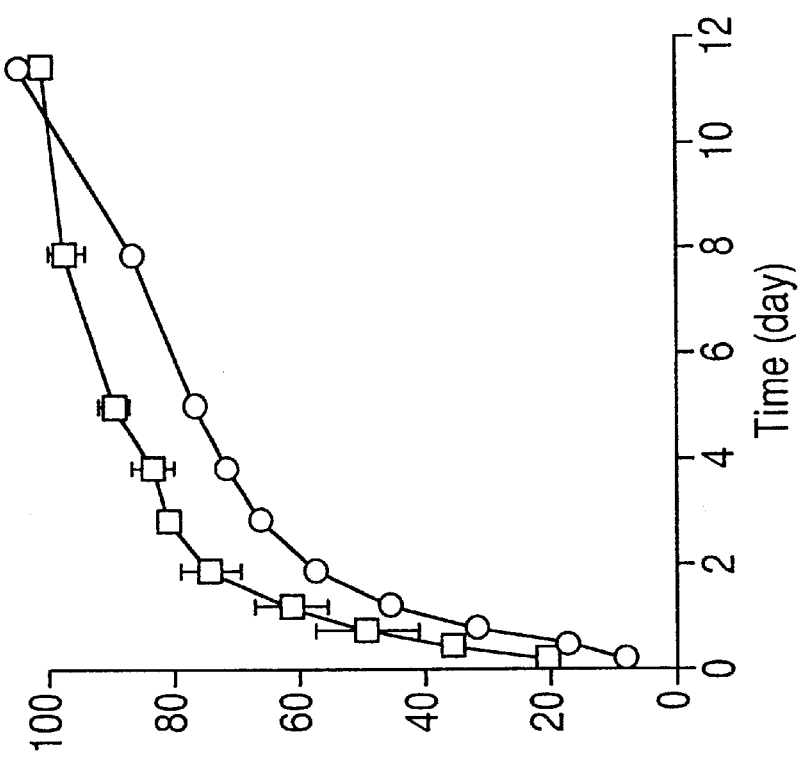
FIG. 5. Release of MTX-dextrans from p(FAD:SA) pellets. The cumulative percentage released (by weight) for MTX (○) and dextran (□) is plotted versus time for polymer pellets containing MTX-amide-dextran FIG. 5(a) and MTX-ester-dextran FIG. 5(b). Points, mean value obtained for three identical polymer pellets. Bars, SD.
Figure 5A:
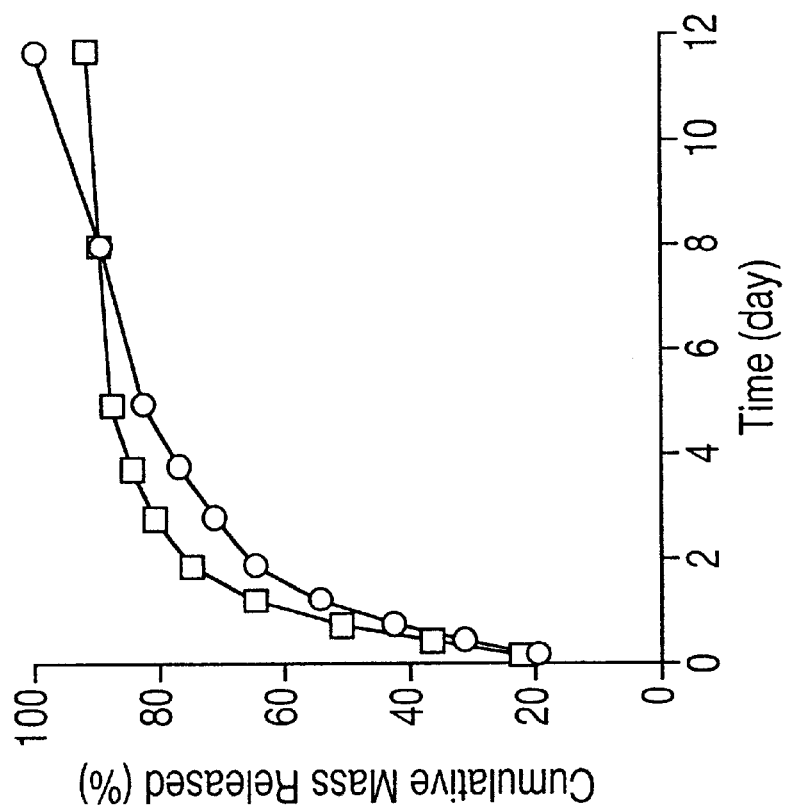

Polymer matrices were prepared by dispersing drug particles within a biodegradable polyanhydride matrix composed of p(FAD:SA). MTX-dextran conjugates were slowly released during incubation in PBS (FIG. 5). The release profiles of MTX and dextran were nearly identical. Two different assay systems, UV absorbance at 305 nm and MTX enzyme inhibition, yielded identical quantities of MTX release (FIG. 6), suggesting that all the released MTX was still biologically active.

Methods: Polymeric pellets were fabricated to contain 90% p(FAD:SA) [polyanhydride copolymer of fatty acid and sebacic acid dimer (1:1)] and 10% of either MTX-dextran conjugate particles or a mixture of MTX and $M_r$ 70,000 unmodified dextran particles (Dang, et al., 1992, *Biotechnol. Prog.*, 8:527–532). These pellets were submerged in 1 ml PBS and incubated at 37° C. with constant shaking. At specific time intervals, the PBS was replaced, and the old solution was stored in the refrigerator for further analysis. Concentration of MTX in the old solution was determined by measuring UV absorbance at 305 nm (Ellaithy, et al., 1983, *Anal. Lett.* 16:1321–1334). The biological activity of released MTX was determined by an enzyme inhibition assay (Kelly, M. G., 1988, *Ann. Clin. Biochem.*, 25:516–521; Yap, et al., 1986, Rapid and inexpensive enzyme inhibition assay of methotrexate, *J. Pharmacol. Methods*, 16:139–150). The concentration of released dextran was determined by carbohydrate assay (Dubois, et al., 1956, Colorimetric method for determination of sugars and related substances, *Anal. Chem.*, 28:350–356).

Example 3

This example demonstrates the cytotoxicity of drug-polymer conjugate against tumor cells in vitro.

MTX and MTX-dextran conjugates were cytotoxic, as demonstrated by observing colony formation following 24-h exposure to H80 cells (FIG. 7). The cytotoxicity of MTX-amide-dextran and MTX-ester-dextran appeared different when compared as a function of total conjugate concentration (FIG. 7*a*). However, when normalized to an equivalent MTX basis, the cytotoxicity of the MTX-dextran conjugates was the same as free MTX (FIG. 7*b*).

Methods: Human glioma cell line (H80) was maintained in improved minimal essential medium-zinc option medium supplied with 10% fetal bovine serum (Gibco, Gaithersburg, Md.). H80 cells were plated in 6-well plates at a density of 500–10,000 cells/ml. Cells were incubated overnight at 37° C. in a humidified 5% $CO_2$ atmosphere and then exposed to various concentrations of MTX or MTX-dextran conjugates in culture medium for 24 h. The medium was replaced with fresh medium after washing the plates with sterilized PBS 2–3 times. The cells were incubated for an additional 5 days and stained with Coomassie blue; colonies that formed were counted. MTX or MTX-dextran concentration required to achieve 50% of cell growth inhibition was determined.

Example 4

This example demonstrates the diffusion of free drug and drug-polymer conjugates in cell-suspended hollow fiber.

Figure 8:
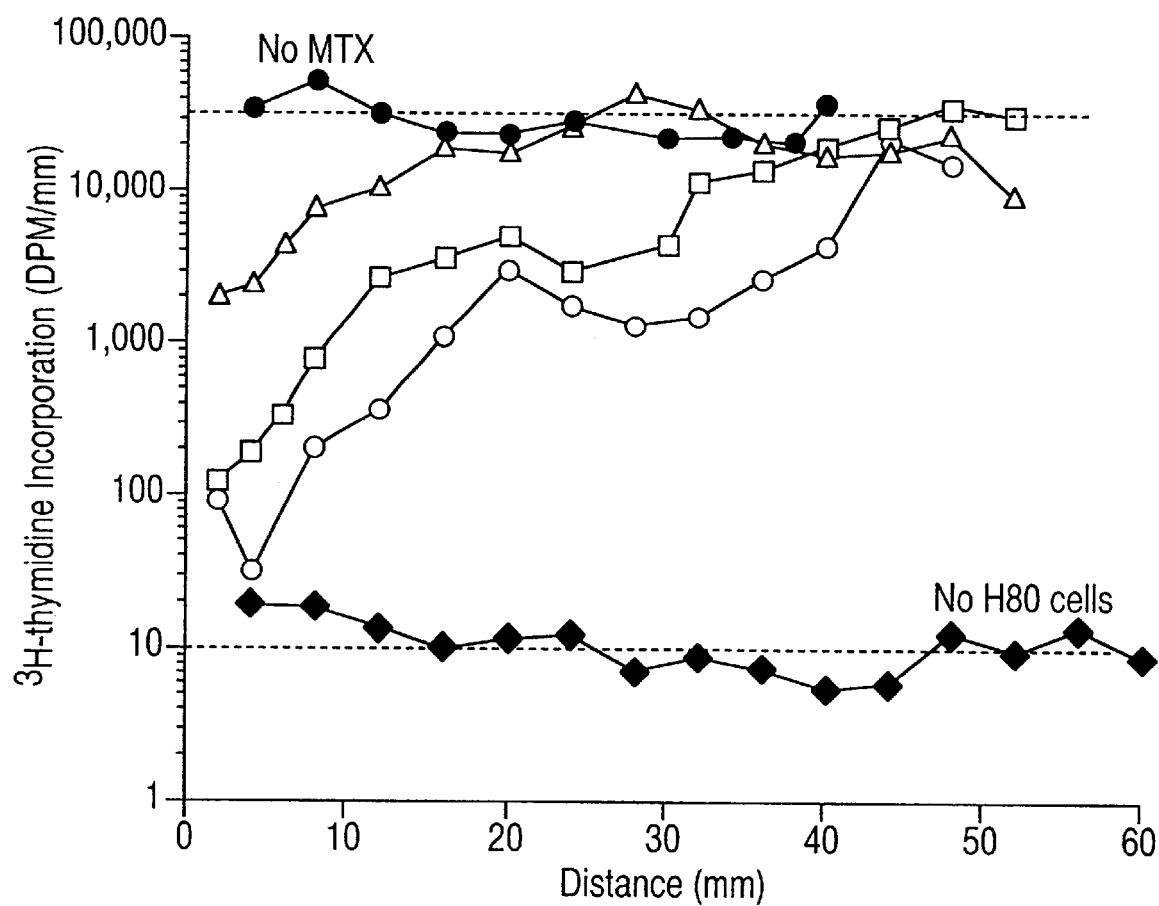
FIG. 8. H80 cell proliferation in a three-dimensional culture system (see FIG. 1) when exposed to different concentrations of methotrexate. H80 cells suspended in an agarose gel were injected into the lumen of a polysulfone microporous hollow fiber. Methotrexate in agarose was added to one end of the fiber at 0.0 μg/ml (●, control), 0.4 μg/ml (Δ), 1.0 μg/ml (□), or 2.0 μg/ml (○). The entire hollow fiber assembly was incubated in cell culture medium at 37° C. for days. Cell proliferation as a function of distance from the drug source was analyzed by measuring the incorporation of [$^3$H]thymidine. For comparison, control experiments were also performed with no cells in the agarose gel (♦).
Figure 9:
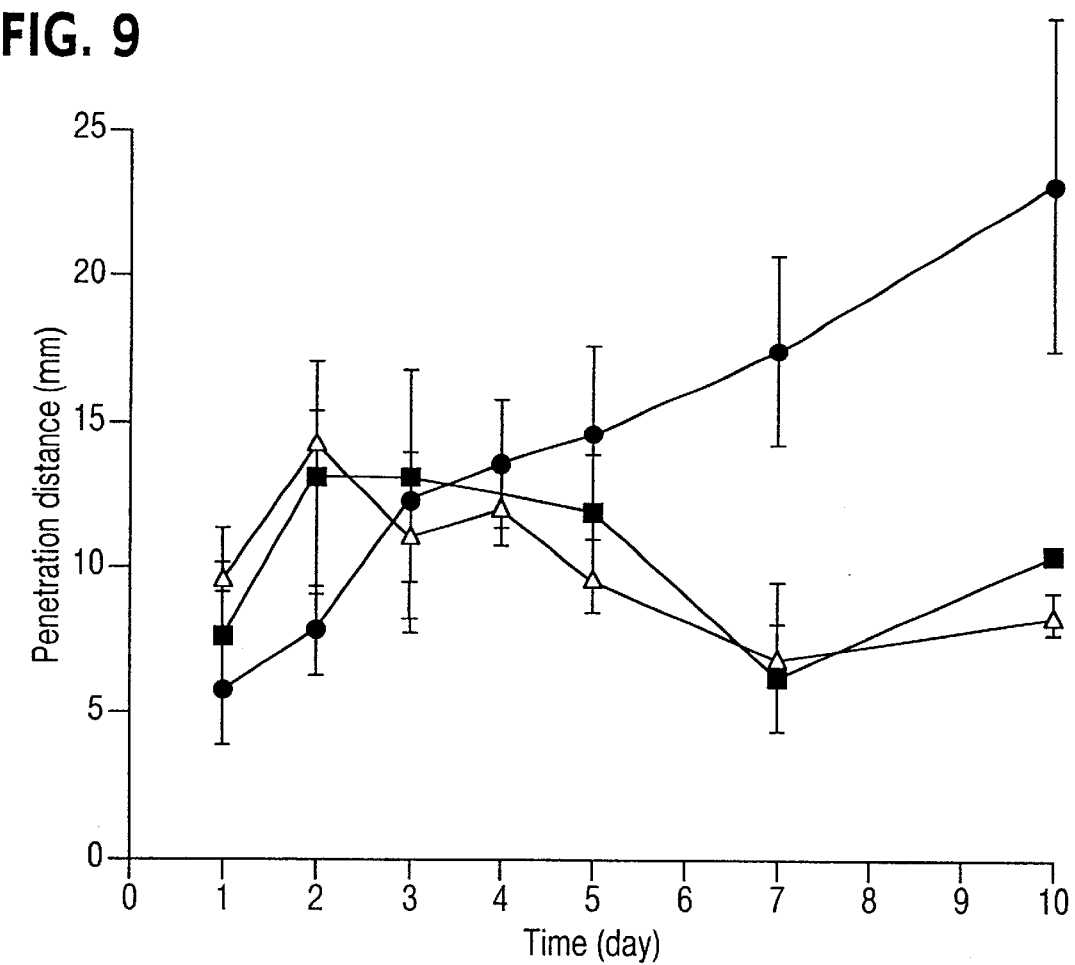
FIG. 9. Penetration of MTX (Δ), MTX-amide-dextran (●), and MTX-ester-dextran (■) into a three-dimensional culture of H80 cells as a function of exposure time. MTX and MTX-dextran conjugates were placed at one end of the cell-populated hollow fiber at 0.4 μg MTX/ml. The fiber was incubated in cell culture medium at 37° C., and [$^3$H] thymidine incorporation as a function of distance in the fiber was determined at various times. Penetration distance was defined as the distance from the drug source where dpm/mm was significantly decreased when compared to dpm/mm in the absence of drug (2× the coefficient of variation). Two or three identically treated fibers were included for each measurement. Points, mean penetration distance; bars, SE (for n=3) or the range (for n=2).

MTX was effective in inhibiting H80 cell proliferation in a three-dimensional matrix, as indicated by the decrease in [$^3$H]thymidine incorporation within the fiber (FIG. 8). The distance of penetration of cytotoxicity into the gel depended on MTX concentration at the source (FIG. 8). Increasing MTX concentration in the drug source produced more effective inhibition of cell proliferation, which was apparent by the more pronounced decrease in [$^3$H]thymidine incorporation near the drug source and enhanced penetration (FIG. 8). By defining a penetration distance for cytotoxicity, as described below, the spatial and temporal pattern of cytotoxicity released in the gel was obtained. FIG. 9 shows the penetration distance for free MTX, MTX-amide-dextran, and MTX-ester-dextran into three-dimensional H80 cell matrices as a function of incubation time. By linking the active agent MTX to dextran by the more stable amide linkage, active MTX penetrated farther in a three-dimensional cell culture than free MTX, which was particularly apparent after several days of culture (FIG. 9). The differences in penetration distance between amide-bonded MTX-dextran and esterbonded MTX-dextran correlated with the stability of the linkage between drug and carrier in buffered saline; increased stability of the MTX-dextran linkage permitted enhanced penetration into the tissue-like matrix.

Methods: CellPrep Agarose Entrapment Medium was obtained from FMC Bioproducts (Rockland, Me.). Polysulfone microporous hollow fibers with a $M_r$ 10,000 cut-off were obtained from Sepelco (Philadelphia, Pa.).

Sterilization of Hollow Fiber. Hollow fibers were exhaustively rinsed with distilled water to remove glycerin used in the manufacture process and then wetted and sterilized as described previously (Shockley, et al., 1989, *Biotechnol. Bioeng.*, 35:843–849). Briefly, the fiber was rinsed both inside and outside with distilled water followed by isopropyl alcohol and then 4% formaldehyde. After rinsing, fibers were incubated in sterile 4% formaldehyde for at least 12 h. Finally, fibers were exhaustively rinsed with sterile distilled water in a sterile hood. After sterilization, fibers were stored in culture medium until use.

Penetration of MTX and MTX-Dextran Conjugates in Cell-populated Hollow Fibers. To determine the extent of penetration for MTX-dextran conjugates, three-dimensional cell cultures within hollow fibers were prepared (FIG. 1). In separate experiments, we determined that the permeability of the hollow fibers to MTX and dextran was $2 \times 10^{-5}$ and $0.1 \times 10^{-5}$ sec$^{-1}$, respectively (Dang, W., 1993, Engineering drugs and delivery systems for brain tumor therapy, *Ph.D. thesis*, The Johns Hopkins University), giving elimination half-times of 10 and 200 h. CellPrep agarose entrapment medium was heated in a water bath (~60° C.) until it became liquid and maintained at 37° C. H80 cells were suspended in CellPrep gel at a density of $5 \times 10^6$ or $1 \times 10^6$/ml and placed in a sterile 1-ml syringe. The syringe was aseptically connected to one end of a sterile hollow fiber, and the cell suspension was injected into the fiber from bottom to top until fluid reached the other end. MTX (0.4, 1.0, and 2.0 µg/ml) or MTX-dextran conjugates (at 0.4 µg MTX/ml) were dissolved in CellPrep, and ~0.02 ml was injected into the fiber, which was previously filled with cell suspension. Fluorescent microspheres were mixed with drug containing agarose gel to allow identification of the interface between the drug source and the cell-suspended gel. Fluorescent microspheres with an average diameter of 100 µm were obtained from Polysciences, Inc. (Warrington, Pa.). The fiber was disconnected from the syringe, and the two ends of the fiber were sealed with autoclaved vacuum grease and submerged in a tissue culture Petri dish with ~20-ml culture medium. The fiber was incubated at 37° C. in a humidified 5% $CO_2$ atmosphere for a specific period (no incubation, 1, 2, 4, 6, or 9 days). After this period, the medium was replaced with medium containing [$^3$H]thymidine (1 µCi/ml), and incubation continued for 24 h. Incorporation of radiolabel was terminated by replacing the [$^3$H]thymidine containing medium with medium containing 100-fold excess of nonradioactive thymidine, and incubation continued overnight. The fibers were frozen on dry ice and cut into 2-mm sections. Cell proliferation as a function of position within the fiber was quantified by measuring [$^3$H]thymidine incorporation into each 2-mm section. Prior to quantification of [$^3$H]thymidine, each fiber section was examined under a fluorescence microscope to determine the position of the interface between the drug source and the cell suspension. To describe the penetration of active drug into the tumor mass, the penetration distance was defined as the distance from the drug source at which the radioactivity (dpm/mm) had decreased by 2× the coefficient of variation (SD/mean of DPM/mm at baseline) of its baseline level (i.e., the level far from the drug source). To obtain the penetration distance of the active drug, the radioactivity incorporated into each fiber section was counted, the dpm/mm was plotted versus distance from the drug source, and the mean dpm/mm of baseline as well as its SD was calculated.

DNA Assay by [$^3$H]Thymidine Incorporation. Cell proliferation was quantified by measuring [$^3$H]thymidine incorporation (Freshney, et al., 1987, Culture of Animal Cells: A Manual of Basic Techniques, New York: Alan R. Liss, Inc.). Briefly, 0.5 ml of 10% ice-cold trichloracetic acid was added to each section to precipitate DNA. The suspension was centrifuged at 10,000 rpm for 10 min, and the supernatant was discarded. One-half ml of 0.3 N NaOH was added to the sample to dissolve the precipitated DNA, the solution was transferred to 5 ml of scintillant fluid, and the radioactivity was counted on a 1600 TR liquid scintillation analyzer (Packard Instrument Company, Downers Grove, Ill.).

Example 5

This example demonstrates the relative efficacies of a drug-polymer conjugate and free drug, both of which were administered in controlled-release matrices.

Figure 10:
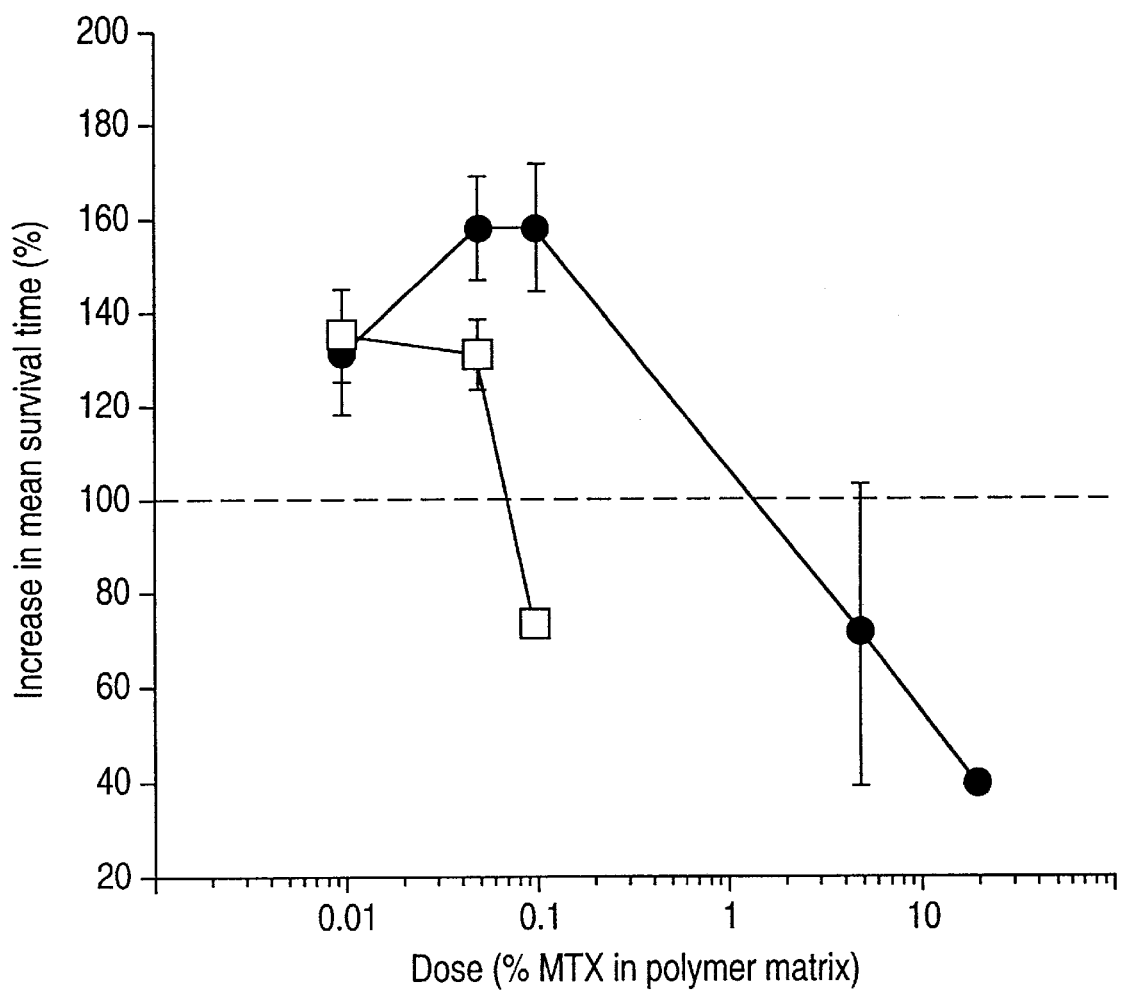
FIG. 10. Survival time (% control) for rats with 9L intracranial tumors as a function of MTX dose in the polymer pellet for MTX (●) or MTX-amide-dextran (□).

MTX and MTX-amide-dextran were effective against 9L gliosarcoma in rat brain, as determined by measuring the survival of tumor-bearing rats that were treated with controlled release polymers containing MTX or MTX-amide-dextran (Table 1). Rats treated with polymers containing only unmodified dextran survived for the same time as control animals. The increase in survival for animals treated with MTX and MTX-amide-dextran over a range of doses is summarized in FIG. 10. Compared with free MTX at low drug loadings in the polymer (0.01%), MTX-amide-dextran conjugate was equally effective in prolonging the survival. However, when the drug loading was high (0.1%), MTX-amide dextran conjugate became toxic, probably due to its slower elimination rate from the brain. With free MTX, toxicity was not observed until much higher doses (~1%; FIG. 10).

Methods: The drug efficacy against brain tumors was tested in a 9L gliosarcoma rat model (Tamargo, et al., 1993, *Cancer Res.*, 53:329–333). Rats were anesthetized by an i.p. injection of 3.0–3.5 ml/kg of freshly prepared anesthetic solution. The anesthesia solution was made by mixing 25 ml of ketamine hydrochloride (100 mg/ml; Park-Davis, Morris Plains, N.J.), 2.5 ml of xylazine (100 mg/ml, Rompun; Mobay Company, Shawnee, Kans.), 14.2 ml of ethanol (100%), and 58.3 ml of sterile saline (0.9% NaCl); this solution was filter sterilized (Corning). Their heads were shaved and prepared in a sterile fashion with 70% ethyl alcohol and povidone-iodine solution. 9L gliosarcoma fragments, grown in the flanks of male Fischer 344 rats, were cut to approximately $2 \times 2 \times 1$ mm$^3$ and kept in physiological saline on ice until implantation. A burr hole was drilled 5 mm posterior to the bregma and 3 mm lateral to the sagittal suture. An incision was made in the dura. The underlying cortex was aspirated gently until the vascular junction between the posterior thalamus and the anterior superior colliculus was exposed. Bleeding was controlled using a sterile Weck-Cel surgical spear (Edward Weck, Inc., Research Triangle Park, N.C.). Once the bleeding stopped, the tumor fragment was transferred into the cortical defect over the brain stem. The wound was irrigated with sterile saline and closed with surgical clips.

On the fifth day after tumor implantation, the rats were randomized to three experimental groups. These animals were anesthetized as described above, the wound clips were removed, and the skin was sterilized. The wound was reopened, and the burr hole was identified. Either a pure p(FAD:SA) pellet (control group), a p(FAD:SA) pellet containing 10% MTX-amide-dextran, or a p(FAD:SA) pellet containing 10% of a mixture of MTX and unmodified dextran-70 was inserted through the craniotomy defect into the cerebral cortex (the absolute concentration of MTX was the same in each pellet). All the polymer pellets were ~2 mm in diameter and ~2 mm in thickness and weighed between 12 and 15 mg. The wound was reclosed with surgical clips, and the animals were returned to their cages and supplied with sufficient food and water. The animals were monitored daily, and the length of survival of each rat following tumor implantation was recorded. The prolongation of life of the test rats was expressed as the ratio of the mean survival time of treated animals to that of the control animals.

Two separate experiments were performed, using different groups of animals with implanted tumors. For each experiment, the loading of the powder in the polymer was 10%. However, the absolute amount of MTX varied. Three different dosages of MTX were tested, 0.1, 0.05 and 0.01% of total polymer pellet weight (1.2, 0.6, and 0.12 μg MTX per 12 mg pellet).

TABLE 1

Mean survival for rats with intracranial 9L glioma treated with p(FAD:SA) pellets containing either MTX-dextran mixtures or MTX-amide-dextran conjugates
All rats were treated 5 days following tumor implantation.

| Particles dispersed in p(FAD:SA) at 10% loading | Dose (% MTX in polymer) | Mean survival time ± SEM (day)[a] (n) | Survival time (% control) |
|---|---|---|---|
| Experiment I | | | |
| None (control group) | | 18.6 ± 2.5 (8) | 100 |
| MTX-amide-dextran | 0.1 | 13.8 ± 0.5 (8) | 74 |
| MTX/dextran mixture | 0.1 | 29.6 ± 2.5 (7) | 160 |
| Experiment II | | | |
| None (control group) | | 14.5 ± 1.9 (8) | 100 |
| Dextran (control group) | | 17.0 ± 1.3 (8) | 117 |
| MTX-amide-dextran | 0.05 | 19.1 ± 1.1 (8) | 132 |
|  | 0.01 | 19.7 ± 1.4 (8) | 140 |
| MTX/dextran mixture | 0.05 | 23.0 ± 1.6 (8) | 160 |
|  | 0.01 | 19.1 ± 1.9 (8) | 132 |

[a]Number in parentheses, the number of rats in each experimental group.

What is claimed is:

1. A multipart drug delivery system for delivering free drug to the extracellular space of a tissue, said multipart drug delivery system providing a reduced rate of drug elimination from its target tissue and an enhanced drug penetration volume from its implantation site relative to free drug and relative to free drug incorporated in a controlled-release matrix, said multipart drug delivery system comprising:

a. a drug covalently attached via a first hydrolytically labile bond to
   b. a water-soluble, high molecular weight first polymer, forming a first drug-polymer conjugate, said conjugate being incorporated in
   c. a controlled-release matrix comprising a biocompatible second polymer.

2. The multipart drug delivery system of claim 1 wherein the first polymer is a polysaccharide.

3. The multipart drug delivery system of claim 2 wherein the polysaccharide is dextran.

4. The multipart drug delivery system of claim 1 wherein the hydrolytically labile bond is an ester bond.

5. A method of performing intrathecal therapy, comprising the step of:

administering directly to an intrathecal space a drug-polymer conjugate, said drug-polymer conjugate providing a reduced rate of drug elimination from its target tissue relative to free drug, said drug-polymer conjugate comprising:
   a. a drug covalently attached via an hydrolytically labile bond to
   b. a water-soluble, high molecular weight polymer wherein said drug is released from said conjugate at a rate providing a $t_{1/2}$ of at least 20 days in PBS at 37° C.

6. The method of claim 5 wherein the polymer is a polysaccharide.

7. The method of claim 6 wherein the polysaccharide is dextran.

8. The method of claim 5 wherein the hydrolytically labile bond is an ester bond.

9. The multipart drug delivery system of claim 1 wherein said drug is released from said conjugate at a rate providing a $t_{1/2}$ of at least 3 days in PBS at 37° C.

10. The multipart drug delivery system of claim 1 wherein said drug is released from said conjugate at a rate providing a $t_{1/2}$ of at least 20 days in PBS at 37° C.

* * * * *